(12) United States Patent
Govari (10) Patent No.: US 10,849,696 B2
(45) Date of Patent: Dec. 1, 2020

(54) MAP OF BODY CAVITY

(71) Applicant: BIOSENSE WEBSTER (ISRAEL) LTD., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 16/289,843

(22) Filed: Mar. 1, 2019

(65) Prior Publication Data

US 2020/0275977 A1 Sep. 3, 2020

(51) Int. Cl.
*A61B 34/20* (2016.01)
*A61B 34/10* (2016.01)
(Continued)

(52) U.S. Cl.
CPC ............ *A61B 34/20* (2016.02); *A61B 5/0035* (2013.01); *A61B 34/10* (2016.02); *A61B 90/37* (2016.02); *G06T 7/0012* (2013.01); *G06T 19/003* (2013.01); *G06T 19/20* (2013.01); *A61B 5/063* (2013.01); *A61B 2034/2063* (2016.02); *A61B 2034/2074* (2016.02); *A61B 2090/368* (2016.02); *A61B 2090/378* (2016.02); *G06K 2209/05* (2013.01); *G06T 7/11* (2017.01); *G06T 15/04* (2013.01); *G06T 15/08* (2013.01); *G06T 17/00* (2013.01); *G06T 2207/10081* (2013.01);
(Continued)

(58) Field of Classification Search
None
See application file for complete search history.

(56) References Cited

U.S. PATENT DOCUMENTS 4,630,203 A 12/1986 Szirtes
7,536,218 B2 5/2009 Govari et al.
(Continued)

FOREIGN PATENT DOCUMENTS

WO WO2018130981 A1 7/2018

OTHER PUBLICATIONS

Soper et al, 'Surface Mosaics of the Bladder Reconstructed From Endoscopic Video for Automated Surveillance', IEEE Trans. on Biomedical Engineering, 59(6), pp. 1670-1680, June. (Year: 2012).*
(Continued)

*Primary Examiner* — Patrick F Valdez (57) ABSTRACT

In one embodiment, a medical analysis system, includes a display, and processing circuitry to receive a three-dimensional map of an interior surface of a cavity within a body of a living subject, positions on the interior surface being defined in a spherical coordinate system wherein each position is defined by an angular coordinate pair and an associated radial distance from an origin, project the angular coordinate pair of respective positions from the interior surface to respective locations in a two-dimensional plane according to a coordinate transformation, compute respective elevation values from the plane at the respective locations based on at least the radial distance associated with the respective projected angular coordinate pair, and render to the display an image of a partially flattened surface of the interior surface with the partially flattened surface being elevated from the plane according to the computed respective elevation values at the respective locations.

17 Claims, 5 Drawing Sheets

(51) Int. Cl.
*A61B 90/00* (2016.01)
*A61B 5/00* (2006.01)
*G06T 7/00* (2017.01)
*G06T 19/00* (2011.01)
*G06T 19/20* (2011.01)
*G06T 7/11* (2017.01)
*A61B 5/06* (2006.01)
*G06T 15/04* (2011.01)
*G06T 15/08* (2011.01)
*G06T 17/00* (2006.01)

(52) U.S. Cl.
CPC ............... *G06T 2207/30032* (2013.01); *G06T 2210/28* (2013.01); *G06T 2210/41* (2013.01)

(56) References Cited

U.S. PATENT DOCUMENTS 7,756,576 B2  7/2010  Levin
2002/0039400 A1  4/2002  Kaufman et al.
2006/0072799 A1*  4/2006  McLain .................. G06T 5/009
                                                            382/128
2010/0303200 A1*  12/2010  Kimchy ................. A61B 5/036
                                                            378/44
2014/0222335 A1*  8/2014  Piemonte ............ G06F 3/04883
                                                            701/527
2015/0049081 A1  2/2015  Coffey et al.
2019/0340838 A1*  11/2019  Gluhovsky ............ A61B 5/068

OTHER PUBLICATIONS

Yingliang Ma et al., "Cardiac Unfold: A Novel Technique for Image-Guided Cardiac Catheterization Procedures", Jun. 27, 2012, Information Processing in Computer-Assisted Interventions, pp. 104-114.

European Search Report for corresponding EPA No. 20160062.4 dated Jun. 30, 2020.

* cited by examiner

MAP OF BODY CAVITY

FIELD OF THE INVENTION

The present invention relates to mapping a body cavity.

BACKGROUND

Medical images of various body parts may be formed in numerous ways for example but not limited to, X-ray radiography, magnetic resonance imaging (MRI), medical ultrasonography or ultrasound, endoscopy, elastography, tactile imaging, thermography, medical photography and nuclear medicine functional imaging techniques.

Volume rendering techniques have been developed to enable computed tomography (CT), MRI and ultrasound scanning software to produce three-dimensional (3D) images for the physician. Traditionally CT and MRI scans produced two-dimensional (2D) static output on film. To produce 3D images, many scans are made, then combined by computers to produce a 3D model, which can then be manipulated by the physician. 3D ultrasounds are produced using a somewhat similar technique.

In attempting to present a 3D image of a body-part, such as a heart chamber, on a 2D screen, manual rotation of the 3D image by means of a user interface allows visual inspection of the various sides of the 3D image by the user.

US Patent Publication 2015/0049081 of Coffey, et al., describes a computer-implemented medical visualization method includes identifying a three-dimensional model of an anatomical item of a particular mammal; automatically identifying an open path in three-dimensional space through the anatomical item; fitting a smooth curve to the open path; and displaying the anatomical item and a visual representation of the smooth curve to a user on a three-dimensional imaging system.

U.S. Pat. No. 4,630,203 to Szirtes describes a method and apparatus for reconstructing the three-dimensional coordinates of an identifiable contour on an object without relying on markers or pre-existing knowledge of the geometry of the object. The technique is defined as Contour Radiography. In the preferred embodiment two X-ray sources irradiate an object possessing a radiographically identifiable contour and then the two images of the contour are projected onto an X-ray film at spaced locations on the film plane. These images are digitized by the tracing of the image curves with a cursor or some other means thereby establishing the coordinates of an arbitrary number of image points. The digital data thus obtained is processed in accordance with a Contour Radiography (CONRAD) algorithm to identify corresponding points on the two curves which originate from the same point on the physical contour. The spatial coordinates of the X-ray sources are determined using a special calibration system. Then the coordinates of each corresponding point pair are processed with the spatial coordinates of the X-ray source to determine the three-dimensional coordinates of their originating space-point on the contour. In this way the three-dimensional coordinates of the contour are determined. The three-dimensional coordinates are then processed in a commercially available graphics system to visually display the reconstructed contour. The technique has particular application in medicine for determining the undistorted shape, position, size and orientation of selected internal organs, such as bone, which have a radiographically identifiable contour.

US Patent Publication 2002/0039400 of Kaufman, et al., describes a system and method for generating a three-dimensional visualization image of an object such as an organ using volume visualization techniques and exploring the image using a guided navigation system which allows the operator to travel along a flight path and to adjust the view to a particular portion of the image of interest in order, for example, to identify polyps, cysts or other abnormal features in the visualized organ. An electronic biopsy can also be performed on an identified growth or mass in the visualized object. Virtual colonoscopy can be enhanced by electronically removing residual stool, fluid and non-colonic tissue from the image of the colon, by employing bowel preparation followed by image segmentation operations. Methods are also employed for virtually expanding regions of colon collapse using image segmentation results.

SUMMARY

There is provided in accordance with an embodiment of the present disclosure, a medical analysis system, including a display, and processing circuitry configured to receive a three-dimensional (3D) map of an interior surface of a cavity within a body of a living subject, positions on the interior surface being defined in a spherical coordinate system wherein each position is defined by an angular coordinate pair and an associated radial distance from an origin of the spherical coordinate system, project the angular coordinate pair of respective positions from the interior surface to respective locations in a two-dimensional (2D) plane a predefined coordinate transformation, compute respective elevation values from the 2D plane at the respective locations based on at least the radial distance associated with the respective projected angular coordinate pair, and render to the display an image of a partially flattened surface of the interior surface of the cavity with the partially flattened surface being elevated from the 2D plane the computed respective elevation values at the respective locations.

Further in accordance with an embodiment of the present disclosure the processing circuitry is configured to add different colors to the partially flattened surface so that the colors are indicative of the computed respective elevation values at the respective locations.

Still further in accordance with an embodiment of the present disclosure the processing circuitry is configured to add contour lines to the partially flattened surface the computed elevation values.

Additionally, in accordance with an embodiment of the present disclosure the processing circuitry is configured to convert for each position, cartesian coordinates of the interior surface to the angular coordinate pair and the associated radial distance.

Moreover, in accordance with an embodiment of the present disclosure the processing circuitry is configured to compute the origin as a centroid of the interior surface.

Further in accordance with an embodiment of the present disclosure the processing circuitry is configured to receive user input indicating end-points for computing a path over the partially flattened surface of the interior surface of the cavity, compute a path between the received end-points responsively to at least some of the computed elevation values, and render the path on the partially flattened surface.

Still further in accordance with an embodiment of the present disclosure, the system includes a medical instrument configured to be inserted into the cavity, and a tracking module configured to track a position of the medical instrument in the cavity, wherein the processing circuitry is configured to render a representation of the medical instrument on the partially flattened surface responsively to the tracked position.

Additionally, in accordance with an embodiment of the present disclosure the processing circuitry is configured to receive user input indicating a new orientation of the partially flattened surface, and render to the display the image of the partially flattened surface with the partially flattened surface being oriented responsively to the new orientation.

There is also provided in accordance with still another embodiment of the present disclosure, a medical analysis method, including receiving a three-dimensional (3D) map of an interior surface of a cavity within a body of a living subject, positions on the interior surface being defined in a spherical coordinate system wherein each position is defined by an angular coordinate pair and an associated radial distance from an origin of the spherical coordinate system, projecting the angular coordinate pair of respective positions from the interior surface to respective locations in a two-dimensional (2D) plane a predefined coordinate transformation, computing respective elevation values from the 2D plane at the respective locations based on at least the radial distance associated with the respective projected angular coordinate pair, and rendering to a display an image of a partially flattened surface of the interior surface of the cavity with the partially flattened surface being elevated from the 2D plane the computed respective elevation values at the respective locations.

Moreover, in accordance with an embodiment of the present disclosure, the method includes adding different colors to the partially flattened surface so that the colors are indicative of the computed respective elevation values at the respective locations.

Further in accordance with an embodiment of the present disclosure, the method includes adding contour lines to the partially flattened surface the computed elevation values.

Still further in accordance with an embodiment of the present disclosure, the method includes converting, for each position, cartesian coordinates of the interior surface to the angular coordinate pair and the associated radial distance.

Additionally, in accordance with an embodiment of the present disclosure, the method includes computing the origin as a centroid of the interior surface.

Moreover, in accordance with an embodiment of the present disclosure, the method includes receiving user input indicating end-points for computing a path over the partially flattened surface of the interior surface of the cavity, computing a path between the received end-points responsively to at least some of the computed elevation values, and rendering the path on the partially flattened surface.

Further in accordance with an embodiment of the present disclosure, the method includes tracking a position of a medical instrument inserted into the cavity, and rendering a representation of the medical instrument on the partially flattened surface responsively to the tracked position.

Still further in accordance with an embodiment of the present disclosure, the method includes receiving user input indicating a new orientation of the partially flattened surface, and rendering to the display the image of the partially flattened surface with the partially flattened surface being oriented responsively to the new orientation.

There is also provided in accordance with still another embodiment of the present disclosure, a software product, including a non-transient computer-readable medium in which program instructions are stored, which instructions, when read by a central processing unit (CPU), cause the CPU to receive a three-dimensional (3D) map of an interior surface of a cavity within a body of a living subject, positions on the interior surface being defined in a spherical coordinate system wherein each position is defined by an angular coordinate pair and an associated radial distance from an origin of the spherical coordinate system, project the angular coordinate pair of respective positions from the interior surface to respective locations in a two-dimensional (2D) plane a predefined coordinate transformation, compute respective elevation values from the 2D plane at the respective locations based on at least the radial distance associated with the respective projected angular coordinate pair, and render to a display an image of a partially flattened surface of the interior surface of the cavity with the partially flattened surface being elevated from the 2D plane the computed respective elevation values at the respective locations.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

As mentioned above, in attempting to present a 3D image of a body-part, such as a heart chamber, on a 2D screen, manual rotation of the 3D image by means of a user interface allows visual inspection of the various side of the 3D image by the user. This type of inspection is limited as all the surfaces of the chamber are generally not visible at the same time, making it difficult for a physician to find a feature of the body-part, and also making it difficult for the physician to appreciate the whole body-part in context. The above-mentioned drawbacks may lead to slower medical procedures or even medical mistakes, which in cardiac, or similar, medical procedures could be fatal.

Embodiments of the present invention partially flatten a 3D map of an interior surface of a 3D cavity within a body of a living subject yielding an intuitive partially flattened surface. The partially flattened surface approximates to a plane with elevations and depressions that represent various projections, indentations and the general shape of the interior surface of the cavity. The partially flattened surface allows opposite sides of the interior surface of the cavity to be viewed at the same time without needing to rotate the image of the partially flattened surface. The partially flattened surface therefore allows the physician to appreciate the whole cavity in context without having to rotate the partially flattened surface. Additionally, the partially flattened surface allows the physician to more easily find a feature of the cavity.

Positions of the interior surface of the cavity of the 3D map are defined in a spherical coordinate system. Each position is defined by an angular coordinate pair $(\theta,\phi)$ and an associated radial distance, r, from an origin of the spherical coordinate system. The origin of the spherical coordinate system may be computed as a centroid of the cavity or defined as some other suitable location. In some embodiments, the 3D map may be first defined by a cartesian, or other, coordinate system, which is then converted to the spherical coordinate system.

The angular coordinate pair $(\theta,\phi)$ of respective positions from the interior surface are projected to respective locations (x,y) in a 2D plane according to a predefined coordinate transformation. So for example, an angular coordinate pair $(\theta_1,\phi_1)$ may be mapped to a location $(x_1,y_1)$ in the 2D plane. The projections may be performed according to any suitable coordinate transformation. The projections and suitable coordinate transformations are described in more detail in the system description below.

Respective elevation values from the 2D plane at the respective locations (x,y) are computed based on at least the radial distance, r, associated with the respective projected angular coordinate pair $(\theta,\phi)$. So for example, the elevation value at location $x_1,y_1$ in the 2D plane is computed based on the radial distance $r_1$ associated with the projected angular coordinate pair $(\theta_1,\phi_1)$. The elevation value at a location may be computed by multiplying R by a given factor, where R is equal to the associated radial distance r, or the associated radial distance, r, less an average radial distance of the positions on the interior surface of the cavity, or the associate radial distance, r, less a minimum radial distance of the positions on the interior surface of the cavity, by way of example only. The elevations may extend above and/or below the 2D plane (i.e., elevations or depressions) depending on how the respective elevation values are computed from the respective radial distances.

An image of the partially flattened surface of the interior surface of the cavity is rendered to a display with the partially flattened surface being elevated from the 2D plane (above and/or below) according to the computed respective elevation values at the respective locations.

Additionally, or alternatively, different colors may be added to the partially flattened surface so that the colors are indicative of the computed respective elevation value ranges at the respective locations. The colors aid the physician to perceive the different elevations and depressions of the partially flattened surface especially when the partially flattened surface is viewed directly from above (e.g., plan view).

Additionally, or alternatively, contour lines may be added to the partially flattened surface according to the computed elevation values. The contour lines also aid the physician to perceive the different elevations and depressions of the partially flattened surface especially when the partially flattened surface is viewed directly from above (e.g., plan view).

The partially flattened surface may be manipulated by the physician so that the surface is viewable at a variety of different orientations. In particular, some orientations enable the physician to see more of the elevations (and/or depressions) in the surface. In this regard, user input may be received indicating that a user has selected a new orientation of the partially flattened surface. The image of the partially flattened surface is then processed and rendered with the partially flattened surface being oriented responsively to the new orientation.

The partially flattened surface may enable better route planning for moving a medical instrument over the interior surface and/or viewing the position of the medical instrument with respect to the interior surface.

The colors and/or the contour lines may also allow the physician to plan a path between two end-points while avoiding elevations and depressions.

Additionally, or alternatively, user input may be received from a user, indicating end-points for computing a path over the partially flattened surface of the interior surface of the cavity. A path between the received end-points may then be computed responsively to at least some of the computed elevation values so that the computed path avoids deviations in elevation above a given limit. The path may then be rendered on the partially flattened surface.

In some embodiments, a position of a medical instrument in the cavity may be tracked using any suitable position tracking technology. A representation of the medical instrument may then be rendered on the partially flattened surface responsively to the tracked position.

System Description

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Figure 1:
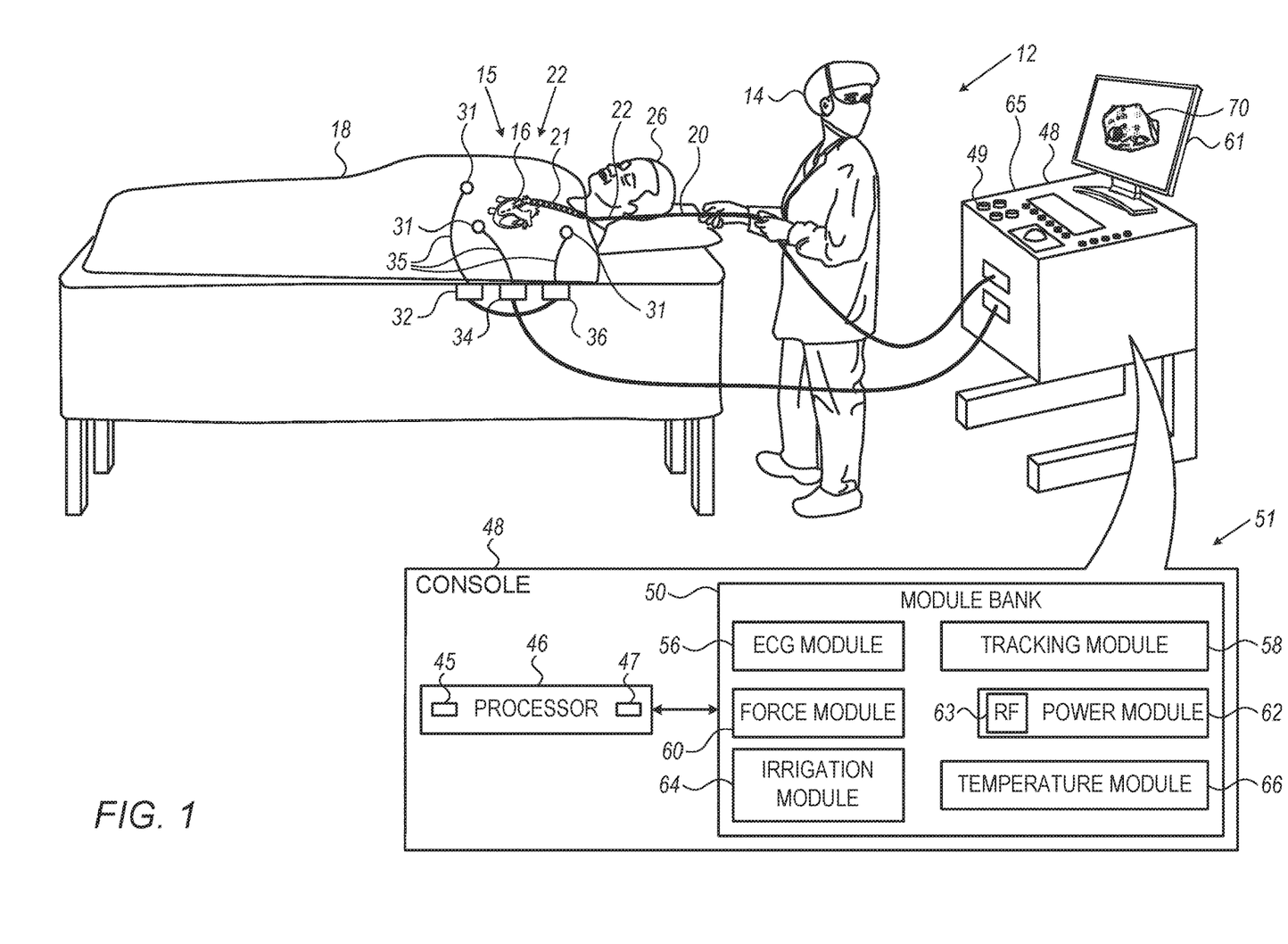
FIG. 1 a schematic illustration of an invasive medical procedure using an apparatus according to an embodiment of the present invention.
Figure 2:
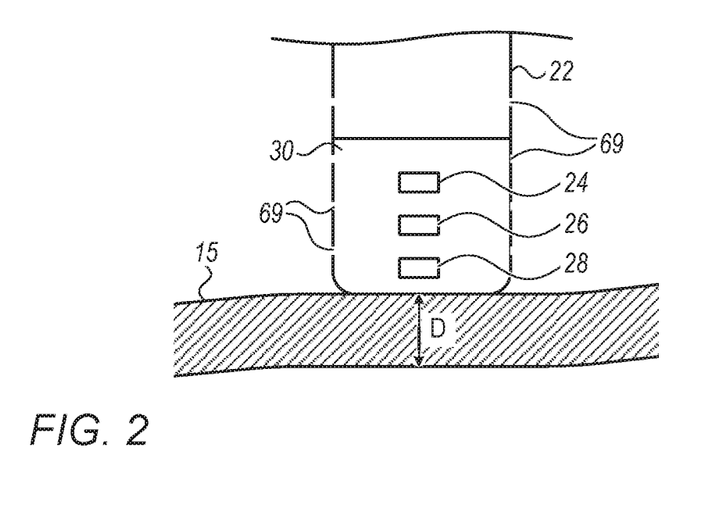
FIG. 2 is a schematic illustration of a distal end of a probe used in the apparatus of FIG. 1 according to an embodiment of the present invention.

Reference is now made to FIG. 1, which is a schematic illustration of an invasive medical procedure using an apparatus 12 including a medical analysis subsystem according to an embodiment of the present invention. Reference is also made to FIG. 2, which is a schematic illustration of a distal end 22 of a probe 20 used in the apparatus 12 according to an embodiment of the present invention. The procedure is performed by a physician 14, and in the description hereinbelow, the procedure is assumed to comprise an ablation of a portion of tissue 15 of a myocardium 16 of the heart of a human patient 18.

In order to perform the investigation, the physician 14 inserts the probe 20 into a sheath 21 that has been pre-positioned in a lumen of the patient 18 so that the probe 20 is inserted into a chamber of the heart. The sheath 21 is positioned so that the distal end 22 of the probe 20 enters the heart of the patient 18. The distal end 22 comprises a position sensor 24 that enables the location and orientation of the distal end 22 to be tracked, a force sensor 26 that measures the force applied by the distal end 22 when it contacts the myocardium 16, and one or more temperature sensors 28 that measure the temperature at respective locations of the distal end 22. The distal end 22 also comprises one or more electrodes 30 which are used to apply radiofrequency power to the myocardium 16 in the chamber so as to ablate the myocardium 16. The electrode(s) 30 may also be used to acquire electropotentials from the myocardium 16.

The apparatus 12 is controlled by a system processor 46, which is located in an operating console 48 of the apparatus. The operating console 48 comprises controls of at least one user input device 49 which are used by the physician 14 to communicate with the processor 46. The software for processor 46 may be downloaded to the processor 46 in electronic form, over a network, for example. Alternatively, or additionally, the software may be provided on non-transitory tangible media, such as optical, magnetic, or electronic storage media.

The processor 46 may comprise real-time noise reduction circuitry 45, typically configured as a field programmable gate array (FPGA), followed by an analog-to-digital (A/D) signal conversion integrated circuit 47. The processor 46 can pass the signal from the A/D signal conversion integrated circuit 47 to another processor and/or can be programmed to perform at least one algorithm disclosed herein, the algorithm comprising steps described hereinbelow. The processor 46 uses the noise reduction circuitry 45 and the A/D signal conversion integrated circuit 47, as well as features of modules which are described in more detail below, in order to perform the algorithm.

In order to operate the apparatus 12, the algorithm of the processor 46 communicates with a module bank 50, which has a number of modules used by the processor 46 to operate the apparatus 12. Thus, the module bank 50 comprises an electrocardiograph (ECG) module 56 coupled to receive signals from body surface electrodes 31 and/or electrodes 30, in order to provide the ECG signals to the processor 46. The body surface electrodes 31 and/or the electrode(s) 30 are configured for application to a body of a subject (e.g., the patient 18) and configured to output signals in response to electrical activity of a heart of the subject. The electrode(s) 30 is applied to the heart of the body via the probe 20. The module bank 50 also includes a tracking module 58 which receives and analyzes signals from the position sensor 24, and which uses the signal analysis to generate a location and an orientation of the distal end 22. In some embodiments the position sensor 24 comprises one or more coils which provide the sensor signals in response to magnetic fields traversing the coils. In these embodiments, in addition to receiving and analyzing signals from sensor 24, tracking module 58 also controls radiators 32, 34, and 36 which radiate the magnetic fields traversing the position sensor 24. The radiators 32, 34, 36 are positioned in proximity to the myocardium 16, and are configured to radiate alternating magnetic fields into a region in proximity to the myocardium 16. A plurality of wire connections 35 link the operating console 48 with body the surface electrodes 31 and other components (such as the radiators 32, 34, 36 and the sensor 24) to enable the tracking module 58 to measure location and orientation coordinates of the probe 20. In some embodiments, the tracking module 58 is configured to compute a relative location and a relative orientation of the probe 20 with respect to the heart. Magnetic location and orientation tracking is described in U.S. Pat. Nos. 7,756,576 and 7,536,218, which are hereby incorporated by reference. The Carto system produced by Biosense Webster, of 33 Technology Drive, Irvine, Calif. 92618 USA, uses such a magnetic tracking system. The tracking module 58 is not limited to using magnetic based location and orientation tracking. Any suitable location and orientation tracking can be used, such as impedance-based or image-based tracking.

The apparatus 12 may receive image data from an external imaging modality, such as an MRI unit, CT unit or the like and includes image processors that can be incorporated in or invoked by the processor 46 for generating and displaying images. The image data may be registered with the tracking module 58 and a user interface screen 70 combining the received data and positions of the probe 20 may be displayed to the physician 14 on a display 61. For example, the track of the distal end 22 of the probe 20 may be shown on a three-dimensional (3D) representation of the heart of patient 18 that is displayed on the display 61. In some embodiments, the 3D representation of the heart may be at least partially computed based on mapping performed by the probe 20.

The electrode(s) 30 and the body surface electrodes 31 may be used to measure tissue impedance at the ablation site as taught in U.S. Pat. No. 7,536,218, issued to Govari et al., which is herein incorporated by reference.

The module bank 50 also comprises a force module 60, a power module 62, an irrigation module 64, and a temperature module 66. The functions of these modules are explained below. The modules in the module bank 50, and the processor 46, are herein termed processing circuitry 51.

The force module 60 receives signals from the force sensor 26, and from the signals generates a magnitude of the contact force, herein assumed to be measured in grams, exerted by the distal end 22 on the tissue 15. In some embodiments the force sensor 26 is configured so that the signals it provides to the force module 60 enable the force module 60 to evaluate a direction of the force exerted by the distal end 22 on the tissue 15.

The power module 62 comprises a radiofrequency (RF) signal generator 63 which generates the radiofrequency power to be applied by the electrode(s) 30 to ablate the tissue 15 of the myocardium 16. The processor 46 and the power module 62 are able to adjust a power level, herein assumed to be measured in Watts, delivered by the electrode(s) 30, as well as a length of time, measured in seconds, during which the power is delivered.

The irrigation module 64 controls a rate of flow, herein assumed to be measured in mL/min, of irrigation fluid, typically normal saline solution, supplied to the distal end 22 by a pump 65 disposed in the operating console 48. The probe 20 includes an irrigation channel through which to irrigate the myocardium 16. The irrigation fluid is expelled from irrigation holes 69 in the distal end 22. The pump 65 is configured to selectively pump the irrigation fluid into the irrigation channel at an idle rate and at one or more one non-idle rates (higher than the idle rate) according to a status of the ablation procedure.

The temperature module 66 receives a temperature signal provided by the temperature sensor 28 (or by each temperature sensor 28). The temperature signal is indicative of a temperature of the myocardium at a plurality of different times. The temperature module 66 determines the temperatures registered by each of the sensors 28. Typically, in the case of multiple sensors 28 the temperature module 66 determines a mean temperature of the distal end 22. Additionally, in the case of multiple sensors, the temperature module 66 may produce a map of the temperature distribution of the distal end 22.

Reference is now made to FIGS. 3-10, which illustrate generation, manipulation and use of a partially flattened surface 80 (shown in FIGS. 4-8) of an interior surface 72 (shown in FIG. 3) of a cavity within a body of a living subject. The cavity may be any suitable cavity within a body of a living subject, for example, but not limited to, a chamber of a heart or a sinus cavity. An image of the partially flattened surface 80 may be rendered by the apparatus 12 on the display 61 or using any suitable processing and display system and is not limited to being rendered by apparatus 12 on the display 61.

Figure 3:
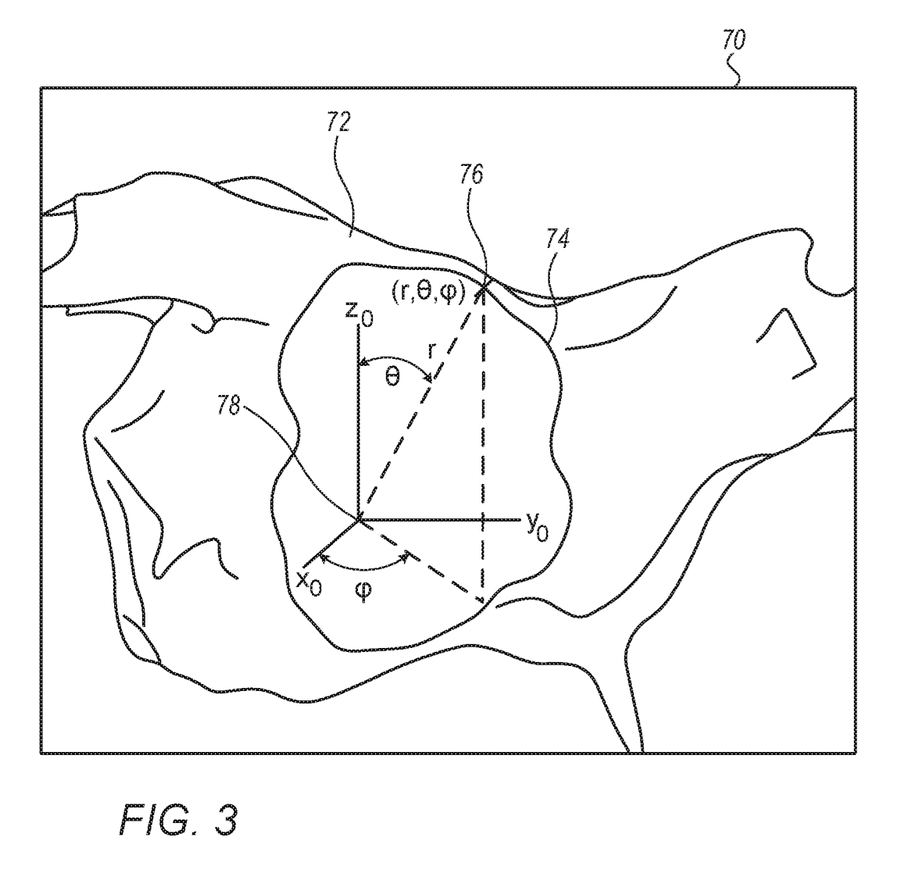
FIG. 3 is a cutaway view of an image of interior surface of a cavity within a body of a living subject received by the apparatus of FIG. 1.

Reference is now made to FIG. 3, which is a cutaway view of an image 70 of the interior surface 72 of the cavity within the body of the living subject received by the apparatus 12 of FIG. 1. In some embodiments, the image 70 may be generated by the apparatus 12. A section 74 has been cut away from the interior surface 72 in order to show how positions 76 (only one shown for the sake of simplicity) are defined. Positions 76 on the interior surface 72 may be defined in a spherical coordinate system wherein each position 76 is defined by coordinates (r,θ,φ), including an angular coordinate pair (θ,φ) and an associated radial distance, r, from an origin 78 of the spherical coordinate system. The polar angle, θ, is measured from a fixed zenith direction ($z_0$ axis in FIG. 3), and the azimuth angle, φ, is measured on a reference plane (defined by the $x_0$ axis and $y_0$ axis) that passes through the origin 78 and is orthogonal to the zenith, measured from a fixed reference direction (from the $x_0$ axis) on that plane. For the sake of convenience, the polar angle, θ, has values from 0 to 180 degrees and the azimuth angle, φ, has values from 0 to 360 degrees. The definition of the ranges covered by the angles θ, φ, may be changed to any suitable range. For example, 0 may be from 0 to 360 and φ may be from −90 to +90 degrees. The angles may also be measured in radians or any suitable unit. In other embodiments, the positions 76 may defined in accordance with any suitable coordinate system.

Figure 4:
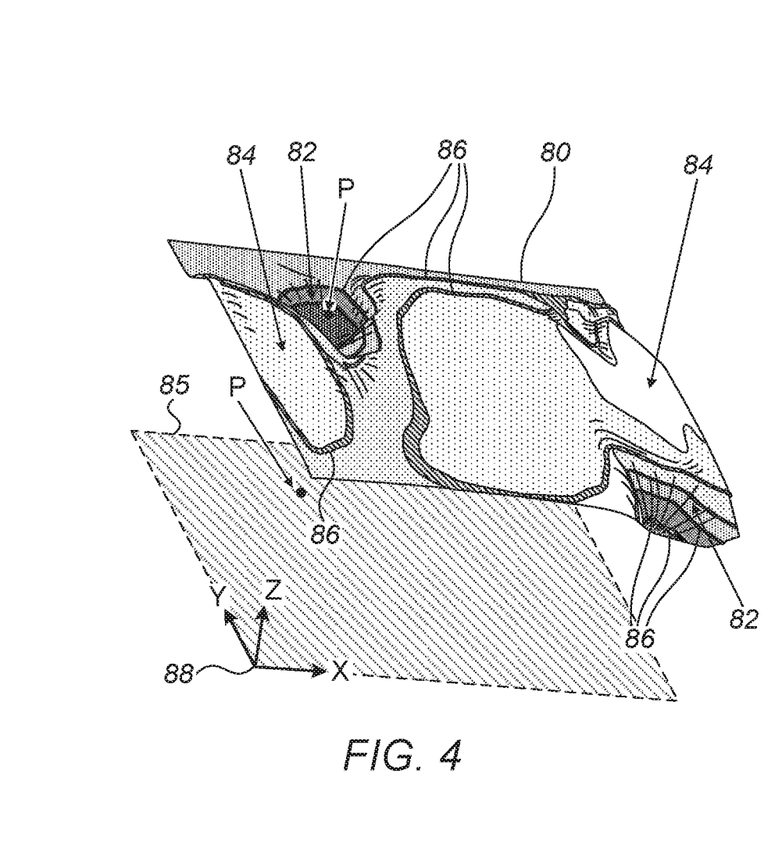
FIG. 4 is a side view of partially flattened surface of the interior surface of the cavity of FIG. 3.

Reference is now made to FIG. 4, which is a side view of the partially flattened surface 80 of the interior surface 72 of the cavity of FIG. 3. The partially flattened surface 80 includes depressions 82 and elevations 84. Computation of the depressions 82 and elevations 84 is now described in more detail.

The angular coordinate pairs (θ,φ) of respective positions 76 (FIG. 3) are projected from the interior surface 72 to respective locations in a 2D plane 85 according to a predefined coordinate transformation. The 2D plane 85 may be defined by an x-axis and a y-axis of a coordinate system 88, e.g., a cartesian coordinate system. So for example, an angular coordinate pair ($\theta_1,\phi_1$) having a radial distance, $r_1$, may be projected to a location ($x_1,y_1$) (according to the coordinate system 88 and also marked as a location P in FIG. 4) in the 2D plane 85.

The projections may be performed according to any suitable coordinate transformation. For example, when the polar angle, θ, has values from 0 to 180 degrees and the azimuth angle, φ, has values from 0 to 360 degrees, the angular coordinate pair may be projected on to a rectangular 2D plane which has x-axis values from 0 to 180 and y-axis values from 0 to 360. The scale of the x-axis and/or y-axis may be linear or non-linear. For each angular coordinate pair (θ,φ), the polar angle, θ, may be projected to the corresponding value of the x-axis and the azimuth angle, φ, may be projected to the corresponding value of the y-axis. For example, an angular coordinate pair of (95°, 280°) is projected to the coordinates (x=95, y=280) of the 2D plane 85.

Other projection methods for projecting positions 76 on the interior surface 72 on to the 2D plane 85 may be used. Projection may differ according to the chosen projection surface (e.g., projection onto a cylinder or a cone), the aspect of the projection (how the interior surface 72 is oriented with respect to the chosen projection surface), scaling used, and choosing a model for the shape of the interior surface 72 (e.g., a sphere or an ellipsoid). Other possible projection methods include Equirectangular, Cassini, Mercator, Miller, Behrmann, Sinusoidal, Eckert, Van der Grinten, by way of example only.

Respective elevation values from the 2D plane 85 at the respective locations (x,y) are computed based on at least the radial distance, r, associated with the respective projected angular coordinate pair (θ,φ). So for example, the elevation value at location P with coordinates $x_j,y_j$ in the 2D plane 85 is computed based on the radial distance $r_1$ associated with the projected angular coordinate pair ($\theta_1,\phi_1$).

The elevation value at a location may be computed by multiplying R by a given scaling factor, where R is equal to one of the following: (a) the associated radial distance r; (b) the associated radial distance, r, less an average radial distance of the positions on the interior surface of the cavity; or (c) the associate radial distance, r, less a minimum radial distance of the positions on the interior surface of the cavity, by way of example only. Depending on the elevation value computation method, the elevation value may result in a positive or a negative value associated with an elevation above or a depression below the 2D plane 85 (parallel to a z-axis of the coordinate system 88), respectively.

For example, if the radial distance is $r_1$, the average radial distance is $r_{av}$, the minimum radial distance is $r_{min}$, and the scaling factor is equal to 0.5, the elevation value may be computed by any of the following methods:

$$0.5 \times r_1; \qquad \qquad 1.$$

$$0.5 \times (r_1 - r_{av}); \text{ or} \qquad \qquad 2.$$

$$0.5 \times (r_1 - r_{min}). \qquad \qquad 3.$$

The partially flattened surface 80 is rendered with the depressions 82 and elevations 84 according to the computed elevation values. In particular, the partially flattened surface 80 is rendered so that positions on its surface are disposed at a distance (measured parallel to the z-axis of the coordinate system 88) from respective locations on the 2D plane 85 equal to the computed respective elevation values of the respective locations. So for example, for an angular coordinate pair ($\theta_1,\phi_1$) having a radial distance, $r_1$, mapped to a location ($x_1,y_1$) in the coordinate system 88 and having a computed elevation value $E_1$, the coordinate of the corresponding position of the partially flattened surface 80 is given by ($x_1, y_1, E_1$) in the coordinate system 88.

Contour lines 86 are also added to the partially flattened surface 80 to highlight lines of equal elevation value and also enable easier identification, by the physician 14, of the depressions 82 and elevations 84 as well as the steepness of the depressions 82 and elevations 84. The granularity of the contour lines may be user definable. In some embodiments, the granularity of the contour lines may be computed by the processor 46 so that the range of elevation values is divided by a given number of contour lines. For example, if the minimum and maximum elevation value is 5 cm and 8 cm, respectively, and the given number of contour lines in 6, the contour lines represent jumps of 0.5 cm in elevation value.

Colors have also been added to the partially flattened surface 80 to indicate different elevation value ranges with different colors. The colors also enable easier identification, by the physician 14, of the depressions 82 and the elevations 84. The elevation value ranges associated with different colors may be user configurable. In some embodiments, the colors may be automatically assigned to different elevation value ranges. Additionally, or alternatively, the number and/or size of the elevation value range may be user configurable.

The partially flattened surface 80 may be manipulated by the physician 14 so that the surface 80 is viewable at a variety of different orientations. In particular, some orientations enable the physician to see more of the elevations (and/or depressions) in the surface. For example, the view of the partially flattened surface 80 is FIG. 4 shows the depressions 82 and elevations 84 more clearly than in the plan view of the partially flattened surface 80 shown in FIG. 5.

Figure 5:
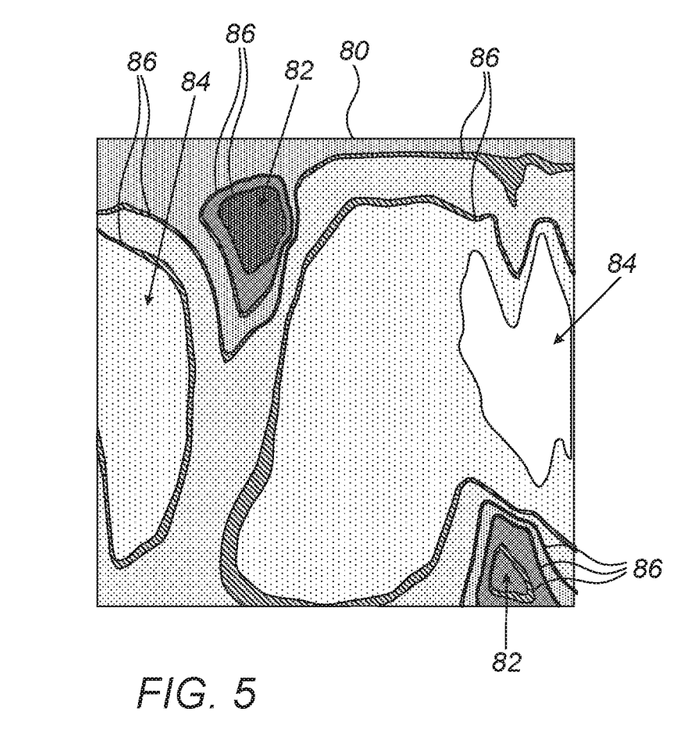
FIG. 5 is a plan view of the partially flattened surface of FIG. 4.

Reference is now made to FIG. 5, which is a plan view of the partially flattened surface 80 of FIG. 4. When viewed from above, the depressions 82 and the elevations 84 may not be as apparent without the use of the colors and or the contour lines 86. The colors and/or the contour lines 86 aid the physician 14 to perceive the different elevations of the partially flattened surface 80 especially when the partially flattened surface is viewed directly from above (e.g., plan view).

Figure 6:
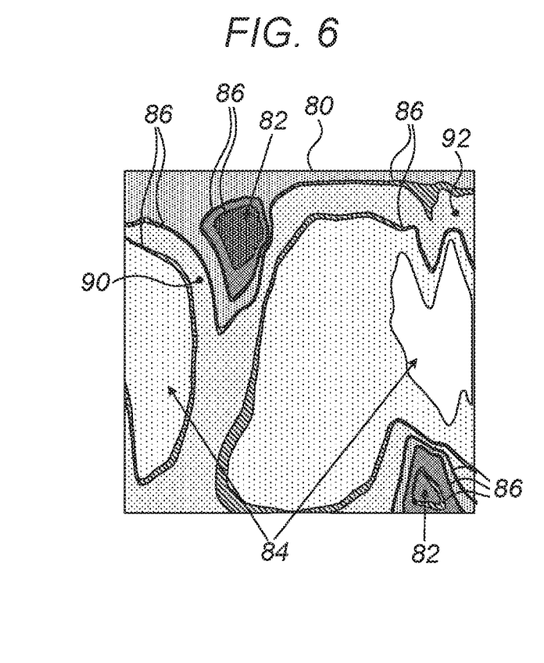
FIG. 6 is a plan view of the partially flattened surface of FIG. 4 including end-points.

Reference is now made to FIG. 6, which is a plan view of the partially flattened surface 80 of FIG. 4 including end-points 90, 92. The end-points 90, 92 may be designated by a user to define a start and end of a desired path across the interior surface 72 of the cavity. The user may want to see a computed path between the end-points 90, 92 based on keeping in the same elevation value range, which may include, for example, any one or more of the following: not crossing one of the contour lines 86, not crossing two of the contour lines 86 etc., and/or not exceeding a given positive and/or negative elevation value during the computed path as a whole or even in a given section or sections of the computed path. The end-points 90, 92 may be input by the user using a suitable user interface screen which shows the partially flattened surface 80 and allows the user to add the end-points 90, 92 to the partially flattened surface 80 using a suitable pointing device, such as a mouse or stylus, by way of example only. The end-points 90, 92 may be added to the partially flattened surface 80 by the user in whichever orientation the partially flattened surface 80 is currently displayed.

Figure 7:
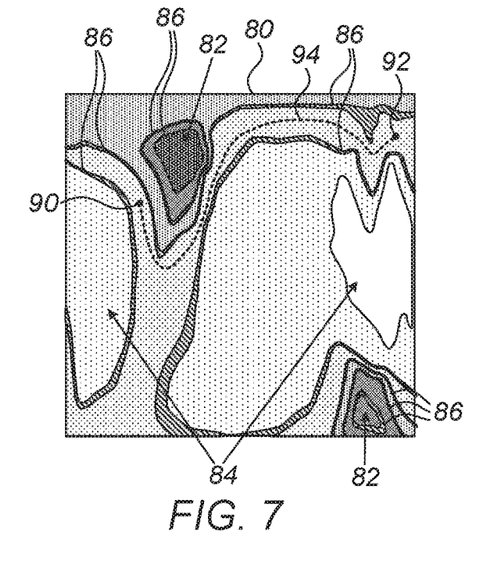
FIG. 7 is a plan view of the partially flattened surface showing a path between the end-points of FIG. 6.

Reference is now made to FIG. 7, which is a plan view of the partially flattened surface 80 showing a path 94 between the end-points 90, 92 of FIG. 6. The path 94 is computed between the end-points 90, 92 based on keeping the path 94 in the same elevation value range, which may include, for example, any one or more of the following: not crossing one of the contour lines 86, not crossing two of the contour lines 86 etc., and/or not exceeding a given positive and/or negative elevation value during the computed path as a whole or even in a given section or sections of the computed path.

Figure 8:
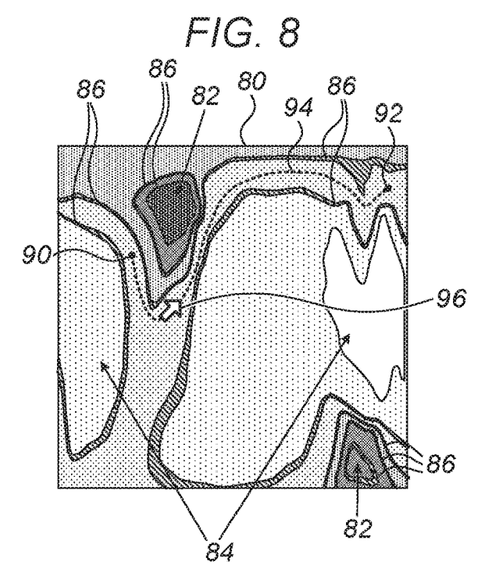
FIG. 8 is a plan view of the partially flattened surface showing a representation of a medical instrument on the path of FIG. 7.

Reference is now made to FIG. 8, which is a plan view of the partially flattened surface 80 showing a representation 96 of a medical instrument on the path 94 of FIG. 7. A position of the medical instrument may be tracked and the tracked position of the medical instrument, with respect to the partially flattened surface 80, may be shown using the representation 96. The representation 96 generally moves as the tracked position of the medical instrument moves.

The probe 20 of FIGS. 1 and 2 is an example of the medical instrument. However, the medical instrument may include any suitable medical instrument such as, a non-ablation probe for inserting into the body-part, an endoscope, and/or a surgical tool such as an ENT tool, suction tool, microdebrider, or shaver, by way of example only.

Figure 9:
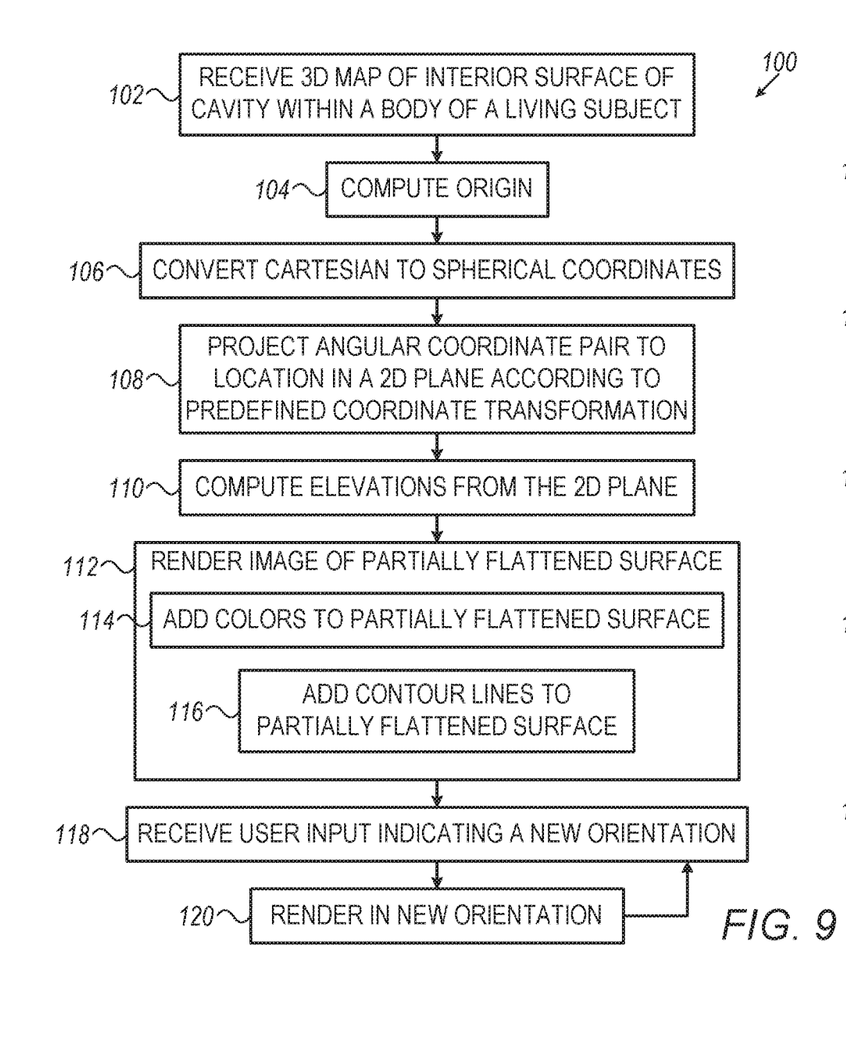
FIG. 9 is a flowchart including exemplary steps in a first method of operation of the apparatus of FIG. 1.

Reference is now made to FIG. 9, which is a flowchart 100 including exemplary steps in a first method of operation of the apparatus 12 of FIG. 1. The processor 46 (FIG. 1) is configured to receive (block 102) a 3D map of the interior surface 72 (FIG. 3) of the cavity within the body of the living subject. The processor 46 is configured to compute (block 104) the origin 78 (FIG. 3) as a centroid of the interior surface 72. In some embodiments, the origin 78 may be any suitable point in, or on, or even outside of, the interior surface 72.

If the interior surface 72 is not yet defined by a spherical coordinate system, the processor 46 is configured to convert (block 106) coordinates (e.g., cartesian coordinates) for positions 76 (FIG. 3) on the interior surface 72 to spherical coordinates with each position 76 being defined by an angular coordinate pair, $(\theta,\phi)$, and an associated radial distance, r, from the origin 78. The processor 46 is configured to project (block 108) the angular coordinate pair, $(\theta,\phi)$, of respective positions 76 from the interior surface 72 to respective locations (x,y) in the 2D plane 85 (FIG. 4) according to a predefined coordinate transformation. The processor 46 is configured to compute (block 110) respective elevation values from the 2D plane 85 at the respective locations based on at least the radial distance, r, associated with the respective projected angular coordinate pair, $(\theta,\phi)$.

The processor 46 is configured to render (block 112) to the display 61 an image of the partially flattened surface 80 (FIGS. 4, 5) of the interior surface 72 of the cavity with the partially flattened surface 80 being elevated from the 2D plane according to the computed respective elevation values at the respective locations. As part of the rendering step of block 112, sub-steps of blocks 114 and/or 116 may be performed. The processor 46 may be configured to add (block 114) contour lines 86 (FIGS. 4 and 5) to the partially flattened surface 80 according to the computed elevation values. The processor 46 may be configured to add (block 116) different colors to the partially flattened surface 80 so that the colors are indicative of the computed respective elevation values at the respective locations.

The processor 46 is configured to receive user input (block 118) indicating a new orientation of the partially flattened surface 80. The processor 46 is configured to render (block 120) to the display 61 the image of the partially flattened surface 80 with the partially flattened surface 80 being oriented responsively to the new orientation.

Figure 10:
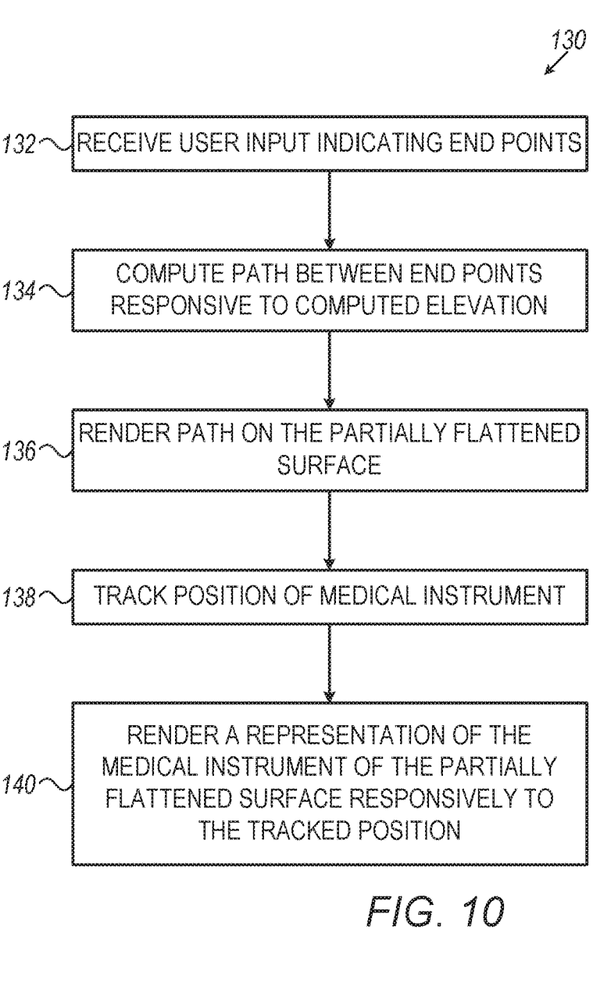
FIG. 10 is a flowchart including exemplary steps in a second method of operation of the apparatus of FIG. 1.

Reference is now made to FIG. 10, which is a flowchart 130 including exemplary steps in a second method of operation of the apparatus 12 of FIG. 1. Reference is also made to FIGS. 6-8.

The processor 46 (FIG. 1) is configured to receive (block 132) user input indicating end-points 90, 92 for computing a path over the partially flattened surface 80 of the interior surface 72 of the cavity. The processor 46 is configured to compute (block 134) the path 94 between the received end-points 90, 92 responsively to at least some of the computed elevation values. In some embodiments, the path 94 is computed between the end-points 90, 92 based on keeping the path 94 in the same elevation value range, which may include, for example, any one or more of the following: not crossing one of the contour lines 86, not crossing two of the contour lines 86 etc., and/or not exceeding a given positive and/or negative elevation value during the computed path as a whole or even in a section of the computed path 94. The processor 46 is configured to render (block 136) the path 94 on the partially flattened surface 80.

In response to a medical instrument being inserted into the cavity, the tracking module 58 is configured to track (block 138) a position of the medical instrument in the cavity. The processor 46 is configured to render (block 140) the representation 96 of the medical instrument on the partially flattened surface 80 responsively to the tracked position.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:

1. A medical analysis system, comprising:
    a display; and
    processing circuitry configured to:
        receive a three-dimensional (3D) map of an interior surface of a cavity within a body of a living subject, positions on the interior surface being defined in a spherical coordinate system wherein each position is defined by an angular coordinate pair and a specific associated radial distance from an origin of the spherical coordinate system;
        project the angular coordinate pair of respective positions from the interior surface to respective locations in a two-dimensional (2D) plane according to a predefined coordinate transformation;
        compute respective elevation values from the 2D plane at the respective locations based on at least a function of the specific associated radial distance associated with the respective projected angular coordinate pair, the elevation values may be positive or negative values associated with an elevation above or a depression below the 2D plane; and
        render to the display an image of a partially flattened surface of the interior surface of the cavity with the partially flattened surface being elevated from the 2D plane according to the computed respective elevation values at the respective locations.

2. The system according to claim 1, wherein the processing circuitry is configured to add different colors to the partially flattened surface so that the colors are indicative of the computed respective elevation values at the respective locations.

3. The system according to claim 1, wherein the processing circuitry is configured to add contour lines to the partially flattened surface according to the computed elevation values.

4. The system according to claim 1, wherein the processing circuitry is configured to convert for each position, Cartesian coordinates of the interior surface to the angular coordinate pair and the associated radial distance.

5. The system according to claim 1, wherein the processing circuitry is configured to compute the origin as a centroid of the interior surface.

6. The system according to claim 1, wherein the processing circuitry is configured to: receive user input indicating end-points for computing a path over the partially flattened surface of the interior surface of the cavity; compute a path between the received end-points responsively to at least some of the computed elevation values; and render the path on the partially flattened surface.

7. The system according to claim 6, further comprising:
    a medical instrument configured to be inserted into the cavity; and
    a tracking module configured to track a position of the medical instrument in the cavity, wherein the processing circuitry is configured to render a representation of the medical instrument on the partially flattened surface responsively to the tracked position.

8. The system according to claim 1, wherein the processing circuitry is configured to: receive user input indicating a new orientation of the partially flattened surface; and render to the display the image of the partially flattened surface with the partially flattened surface being oriented responsively to the new orientation.

9. A medical analysis method, comprising:
    receiving a three-dimensional (3D) map of an interior surface of a cavity within a body of a living subject, positions on the interior surface being defined in a spherical coordinate system wherein each position is defined by an angular coordinate pair and a specific associated radial distance from an origin of the spherical coordinate system;
    projecting the angular coordinate pair of respective positions from the interior surface to respective locations in a two-dimensional (2D) plane according to a predefined coordinate transformation;
    computing respective elevation values from the 2D plane at the respective locations based on at least a function of the specific associated radial distance associated with the respective projected angular coordinate pair, the elevation values may be positive or negative values associated with an elevation above or a depression below the 2D plane; and
    rendering to a display an image of a partially flattened surface of the interior surface of the cavity with the partially flattened surface being elevated from the 2D plane according to the computed respective elevation values at the respective locations.

10. The method according to claim 9, further comprising adding different colors to the partially flattened surface so that the colors are indicative of the computed respective elevation values at the respective locations.

11. The method according to claim 9, further comprising adding contour lines to the partially flattened surface according to the computed elevation values.

12. The method according to claim 9, further comprising converting, for each position, Cartesian coordinates of the interior surface to the angular coordinate pair and the associated radial distance.

13. The method according to claim 9, further comprising computing the origin as a centroid of the interior surface.

14. The method according to claim 9, further comprising:
    receiving user input indicating end-points for computing a path over the partially flattened surface of the interior surface of the cavity;
    computing a path between the received end-points responsively to at least some of the computed elevation values; and
    rendering the path on the partially flattened surface.

15. The method according to claim 14, further comprising: tracking a position of a medical instrument inserted into the cavity; and rendering a representation of the medical instrument on the partially flattened surface responsively to the tracked position.

16. The method according to claim 9, further comprising:

receiving user input indicating a new orientation of the partially flattened surface; and rendering to the display the image of the partially flattened surface with the partially flattened surface being oriented responsively to the new orientation.

17. A software product, comprising a non-transient computer-readable medium in which program instructions are stored, which instructions, when read by a central processing unit (CPU), cause the CPU to:

receive a three-dimensional (3D) map of an interior surface of a cavity within a body of a living subject, positions on the interior surface being defined in a spherical coordinate system wherein each position is defined by an angular coordinate pair and a specific associated radial distance from an origin of the spherical coordinate system;

project the angular coordinate pair of respective positions from the interior surface to respective locations in a two-dimensional (2D) plane according to a predefined coordinate transformation;

compute respective elevation values from the 2D plane at the respective locations based on at least a function of the specific associated radial distance associated with the respective projected angular coordinate pair, the elevation values may be positive or negative values associated with an elevation above or a depression below the 2D plane; and render to a display an image of a partially flattened surface of the interior surface of the cavity with the partially flattened surface being elevated from the 2D plane according to the computed respective elevation values at the respective locations.

* * * * *